US008155430B2

(12) United States Patent
Sato et al.

(10) Patent No.: US 8,155,430 B2
(45) Date of Patent: Apr. 10, 2012

(54) METHOD OF MEASUREMENT OF NUMBER OF NONMETALLIC INCLUSIONS AND CASTING MOLD FOR OBTAINING CAST SAMPLE USED FOR SAME

(75) Inventors: Mitsuyoshi Sato, Toyota (JP); Hiroshi Kawai, Toyota (JP); Yukio Kuramasu, Shizuoka (JP); Ryouji Abe, Shizuoka (JP)

(73) Assignees: Toyota Jidosha Kabushiki Kaisha, Aichi (JP); Nippon Light Metal Company, Ltd., Tokyo (JP)

( * ) Notice: Subject to any disclaimer, the term of this patent is extended or adjusted under 35 U.S.C. 154(b) by 241 days.

(21) Appl. No.: 12/444,724

(22) PCT Filed: Mar. 7, 2008

(86) PCT No.: PCT/JP2008/054698
§ 371 (c)(1),
(2), (4) Date: Apr. 8, 2009

(87) PCT Pub. No.: WO2008/111666
PCT Pub. Date: Sep. 18, 2008

(65) Prior Publication Data
US 2010/0119145 A1 May 13, 2010

(30) Foreign Application Priority Data
Mar. 8, 2007 (JP) ................................ 2007-058423

(51) Int. Cl.
*G06K 9/00* (2006.01)
(52) U.S. Cl. ........................................ 382/152; 382/149
(58) Field of Classification Search .................. 382/149, 382/152
See application file for complete search history.

(56) References Cited

U.S. PATENT DOCUMENTS

| 6,947,588 B2* | 9/2005 | Sim ................................ 382/149 |
| 7,366,344 B2* | 4/2008 | Sim ................................ 382/149 |
| 7,965,883 B2* | 6/2011 | Nishino et al. ................ 382/141 |
| 2006/0228017 A1 | 10/2006 | Kuramasu et al. |

(Continued)

FOREIGN PATENT DOCUMENTS
JP 55-15033 A 2/1980
(Continued)

OTHER PUBLICATIONS

International Search Report of PCT/JP2008/054698 (Jun. 3, 2008).

*Primary Examiner* — Roy M Punnoose
(74) *Attorney, Agent, or Firm* — Millen, White, Zelano & Branigan, P.C.

(57) ABSTRACT

A method of automatically counting a number of inclusions by eliminating the effects of shrinkage cavities in the conventional method and securing a high correlation with a value measured by a skilled worker and a casting mold for obtaining a cast sample used for the same are provided. A method of measurement of a number of nonmetallic inclusions comprising capturing an image of a rectangular fracture surface of a cast sample consisting of an aluminum alloy by a CCD camera or other image capturing means, processing the image captured by the image capturing means for color density, digitalizing the processed image by a predetermined threshold value, and counting the number of pixel clusters of a predetermined size or more, the method characterized by detecting the end edges of the short sides of the rectangular fracture surface before the capturing of its image and automatically setting measurement regions of an area of ¼ to ⅔ of the area of the fracture surface at the two ends of the fracture surface. A casting mold for obtaining a cast sample comprised of a top mold having a recess and a bottom mold having a sprue, having a substantially rectangular parallelepiped cavity extending in the melt flow direction in the state where the top mold and the bottom mold are assembled, and provided, at equal intervals at the bottom of the recess of the top mold with a handle, with inverted V-shaped projections extending in a direction vertical to the melt flow direction.

11 Claims, 6 Drawing Sheets

U.S. PATENT DOCUMENTS

2009/0148014 A1 * 6/2009 Kanda .......................... 382/128

FOREIGN PATENT DOCUMENTS

| JP | 58-35461 A | 3/1983 |
| JP | 7-193709 A | 7/1995 |
| JP | 10-110211 A | 4/1998 |
| JP | 10-170502 A | 6/1998 |
| JP | 2005-189089 A | 7/2005 |
| WO | WO 2004/111619 A1 | 12/2004 |

* cited by examiner

Fig.2
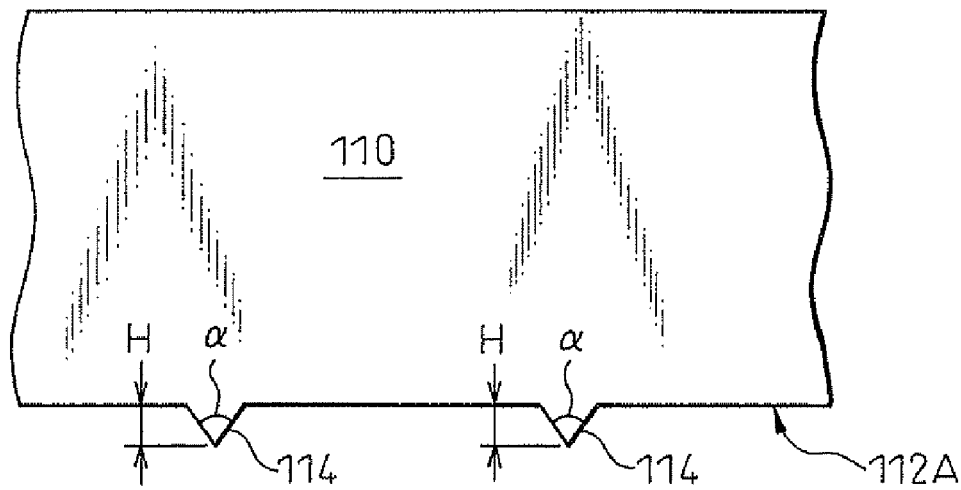
(1)
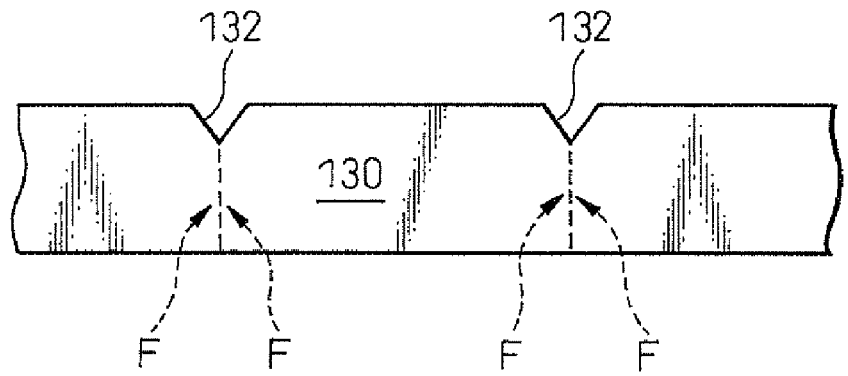
(2)

Fig.4
(1)
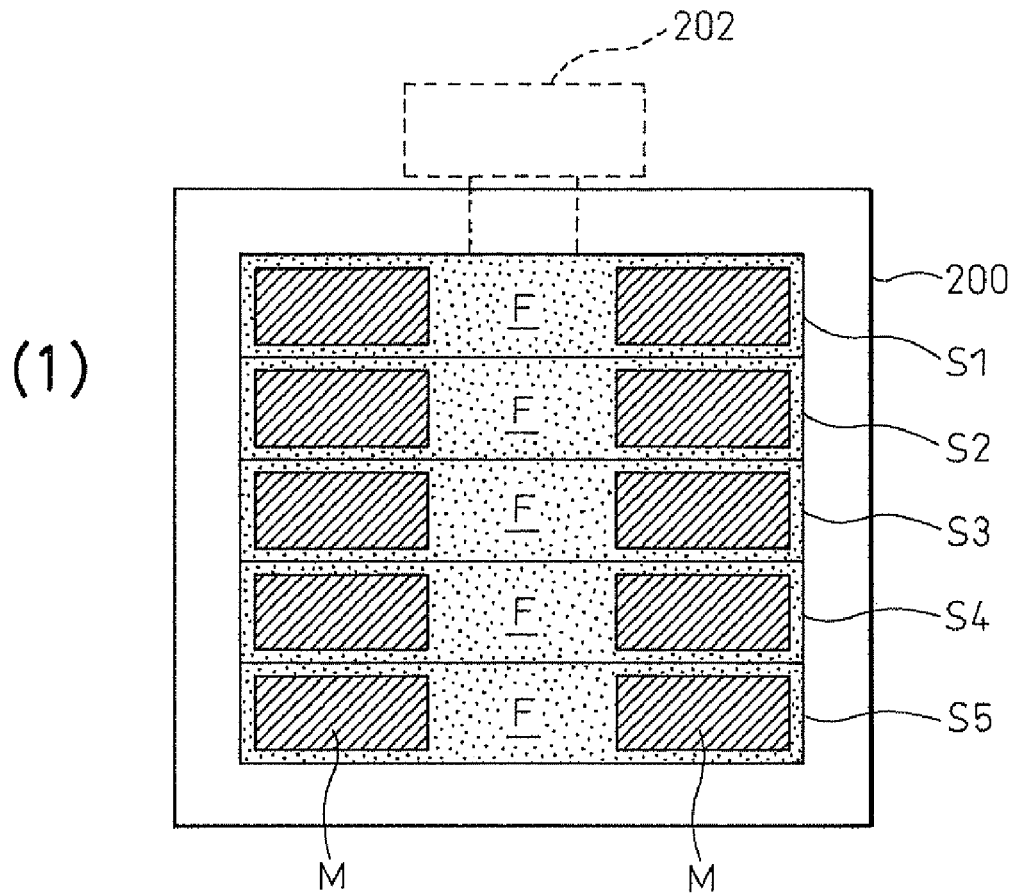
(2)
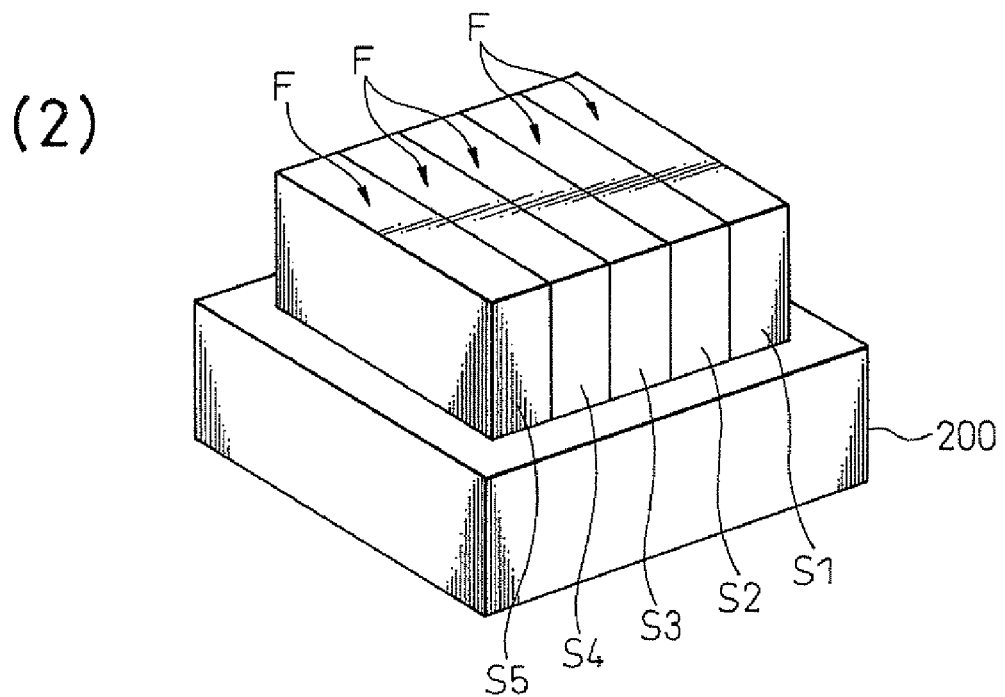

METHOD OF MEASUREMENT OF NUMBER OF NONMETALLIC INCLUSIONS AND CASTING MOLD FOR OBTAINING CAST SAMPLE USED FOR SAME

TECHNICAL FIELD

The present invention relates to a method of measurement of a number of nonmetallic inclusions, more particularly a method of measurement of a number of nonmetallic inclusions comprising capturing an image of a rectangular shaped fracture surface of a cast sample comprised of an aluminum alloy by a CCD camera or other image capturing means, processing the image captured by the image capturing means by color density, digitalizing it by predetermined threshold values, and counting the number of pixel clusters of a predetermined size or more, and a casting mold for obtaining a cast sample used for the same.

BACKGROUND ART

As a method for evaluation of the quality of a melt used for an aluminum alloy casting, the K-mold method is known. According to this method, a relatively small sample of the melt is taken on-site and cast in a K-mold. The fracture surface of the cast sample is observed by the measurer. By counting the number of oxides, pieces of film, and other nonmetallic inclusions, it is possible to quickly inspect the quality (Japanese Utility Model Publication (B2) No. 52-17449: hereinafter referred to as the "old measurement method").

However, the measurer counts the number of nonmetallic inclusions present at the fracture surface by the naked eye or through a magnifying glass, so skill is required. There was therefore the defect that the measurement value differed depending on the measurer.

Therefore, the inventors developed a method of automatically counting the number of inclusions of a predetermined particle size (for example, 100 µm) or more by arranging a sample fracture surface at a special illumination system, using a CCD camera to capture an image of that fracture surface, processing the image for color density, and digitalizing it by predetermined threshold values so as to thereby eliminate the differences in measurement value depending on the measurer and enable easy measurement by a worker on site (Japanese Patent Publication (A) No. 2005-3510: hereinafter referred to as the "conventional automatic measurement method").

However, in counting the number of inclusions by this conventional automatic measurement method as well, the image of the entire area of the sample fracture surface was captured, so even shadows due to fine shrinkage cavities present at the fracture surface ended up being captured in the image. For this reason, there have frequently been cases where the number of inclusions measured by a skilled worker and the number of inclusions measured by the conventional automatic measurement method have remarkably diverged.

DISCLOSURE OF INVENTION

The present invention has as its object the provision of a method for automatically counting the number of inclusions by eliminating the effect of shrinkage cavities in the conventional automatic measurement method and securing high correlation with a value measured by a skilled worker and of a casting mold for obtaining a cast sample used for the same.

The inventors engaged in intensive research and as a result developed an epoch making measurement method eliminating the effects of shrinkage cavities by limiting the regions of the fracture surface captured in the conventional automatic measurement method and thereby completed the present invention.

When an aluminum alloy melt solidifies in a K-mold, cooling of the casting mold results in solidification starting from the surface of the sample. Since the final solidified part becomes the center of the sample, the majority of the shrinkage cavities tend to concentrate at the center of the sample fracture surface. In the conventional automatic measurement method, the image captured from the entire fracture surface of the sample was used, so both the shrinkage cavities present at the sample center and oxides, pieces of film, and other nonmetallic inclusions were detected. For this reason, there was a low correlation between the measurement value obtained by the naked eye of a skilled worker and the measurement value obtained by the conventional automatic measurement method. It was difficult to quickly check the quality of the aluminum alloy melt on-site.

Therefore, to eliminate the effects of these shrinkage cavities, first the image capturing means is used to detect end edges of the fracture surface, and measurement regions of an area of ¼ to ⅔ of the area of the fracture surface are automatically set at the two ends of the fracture surface.

That is, a first aspect of the invention is a method of measurement of the number of nonmetallic inclusions comprising capturing an image of a rectangular fracture surface of a cast sample consisting of an aluminum alloy by a CCD camera or other image capturing means, processing the image captured by the image capturing means for color density, digitalizing the processed image by predetermined threshold values, and counting the number of pixel clusters of a predetermined size or more, the method characterized by detecting the end edges of the short sides of the rectangular fracture surface before the capturing of its image and automatically setting measurement regions of an area of ¼ to ⅔ of the area of the fracture surface at the two ends of the fracture surface.

A second aspect of the invention is a casting mold for obtaining a cast sample used in the first aspect of the invention, the casting mold characterized by comprising a top mold having a recess and a bottom mold having a sprue, having a substantially rectangular parallelepiped cavity extending in the melt flow direction in the state where the top mold and the bottom mold are assembled, and provided, at equal intervals at the bottom of the recess of the top mold, with inverted V-shaped projections extending in a direction vertical to the melt flow direction.

According to the first aspect of the invention, before using the CCD camera to capture an image of the fracture surface of the cast sample, the end edges of the fracture surface are detected and measurement regions of an area of ¼ to ½ of the area of the fracture surface are automatically set at the two ends of the fracture surface, so the image of the shrinkage cavities present at the center of the fracture surface is never incorporated. As a result, by processing the captured image for color density, digitalizing it by predetermined threshold values, and counting the number of pixel clusters of a predetermined size or more, it is possible to more accurately measure the number of oxides, pieces of film, and other nonmetallic inclusions.

According to the second aspect of the invention, inverted V-shaped projections extending in a direction vertical to the melt flow direction are provided at equal intervals at the inside surface of the top mold, so V-notches are formed at equal intervals at the top surface of the cast sample.

If fracturing the cast sample at the portions of the V-notches, it is possible to obtain a plurality of cast sample pieces of substantially the same sizes having flat fracture surfaces. For this reason, in the method of measurement of the number of nonmetallic inclusions of the present invention, accurate measurement of the number of nonmetallic inclusions becomes possible.

BRIEF DESCRIPTION OF THE DRAWINGS

FIG. 2 gives cross-sectional views along the centerline of a total mold of the casting mold shown in FIG. 1 and a cast sample.

FIG. 4 shows a sample comprised of a combination of sample pieces in the method of measurement of the present invention and shows measurement regions in fracture surfaces of the sample pieces.

BEST MODE FOR CARRYING OUT THE INVENTION

Figure 1:
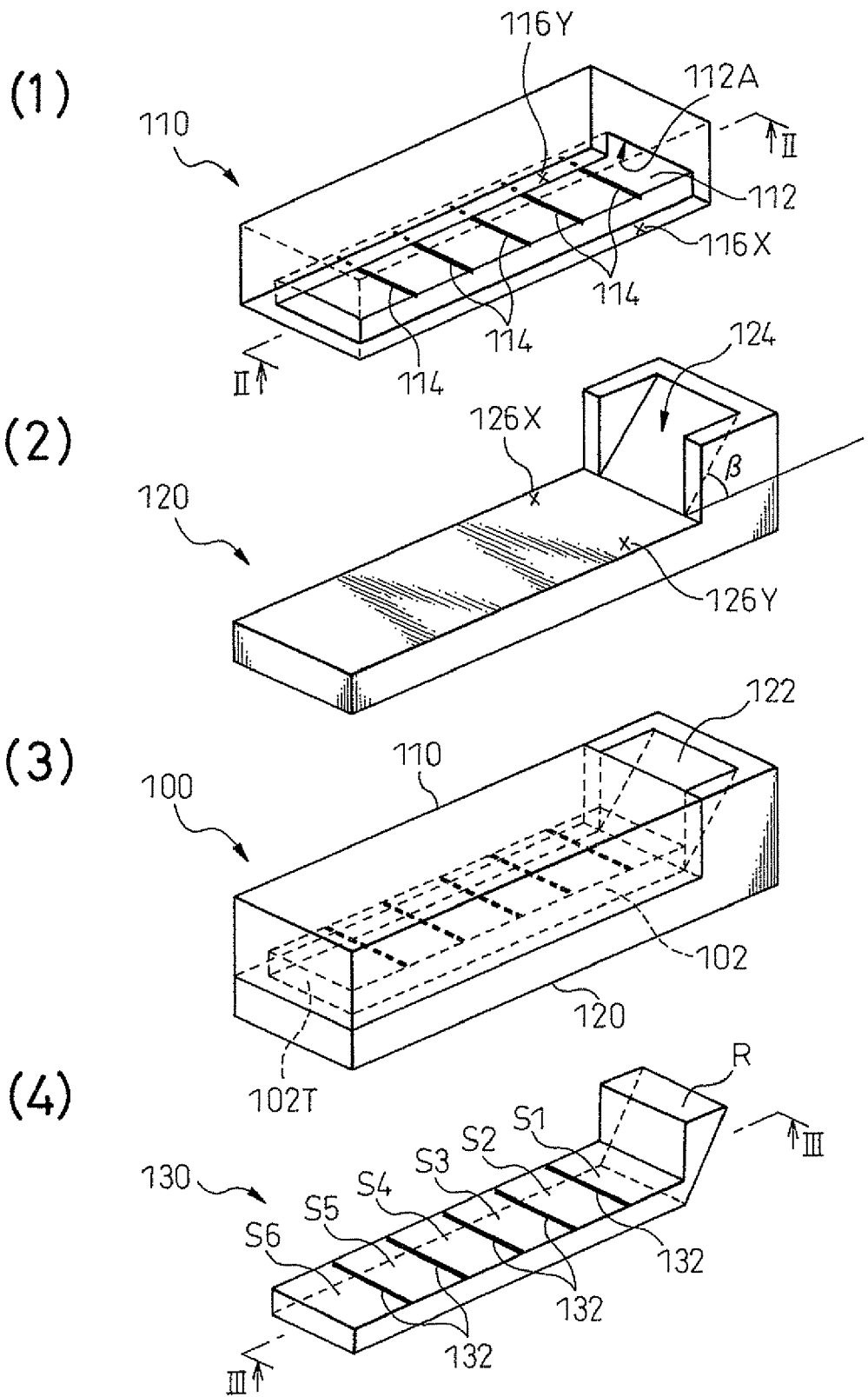
FIG. 1 gives perspective views showing a casting mold for obtaining a cast sample and a cast sample obtained using this used for the method of measurement of the number of inclusions of the present invention.

As explained above, by processing by color density the image of regions of the fracture surface captured from measurement regions of an area of ¼ to ⅔ of the area of the fracture surface, digitalizing this by predetermined threshold values, and counting the number of nonmetallic inclusions with a predetermined particle size (for example, an equivalent circle diameter of 100 μm) or more, it becomes possible to automatically count the number of nonmetallic inclusions per cast sample (hereinafter referred to as the "K value").

When the area of the measurement regions is less than ¼ of the area of the fracture surface, the probability of the shrinkage cavities being incorporated in the image becomes lower, but the area of the measurement regions per fracture surface becomes too small, so accurate measurement requires an increase in the number of cast sample pieces. Preparation of cast sample pieces by obtaining and fracturing a cast sample by a K-mold is troublesome so is not preferable. When the area of the measurement regions exceeds ⅔ of the area of the fracture surface, a smaller number of cast sample pieces is sufficient, but the probability of the shrinkage cavities present at the center of the fracture surface being incorporated in the image becomes higher and measurement of the accurate number of nonmetallic inclusions becomes difficult.

Specifically, the "K value" is found by dividing the number of inclusions counted by a measurer by direct naked eye observation in the range of five cast samples (=10 fracture surfaces) by the five cast samples. Further, the "$K_{10}$ value" is the value found by similarly dividing the number of inclusions measured by a measurer through a 10× magnifying glass in the range of five cast samples (=10 fracture surfaces) by the five cast samples. According to the present invention, the correlation between the value measured by a skilled worker by the naked eye and the value measured by the new automatic measurement method becomes high and a quick check of the quality of an aluminum alloy melt on-site becomes possible.

Here, a "pixel cluster" means a region where adjoining pixels are connected. That is, the pixels may be narrow fiber shapes like with the cross-section of a film-like inclusion when viewed two-dimensionally or may be irregular triangular shapes, diamond shapes, or circular shapes. As special cases, a pixel cluster may include a blank region of pixels. So long as the blank region is surrounded by pixels and the blank region is not connected to the outside matrix, the pixel cluster is treated as being integral even if including this blank region. Here, a "matrix" means a region of the fracture surface with no nonmetallic inclusions, that is, a region excluding only nonmetallic inclusions in the region of the fracture surface captured.

In one preferred embodiment of the first aspect of the invention, pluralities of the measurement regions are set at the inside of the fracture surface and are rectangular in shape.

In this preferred embodiment, pluralities of measurement regions of an area within the above prescribed range are set inside the rectangular shaped fracture surface at the two ends of the fracture surface and are rectangular in shape, so it is possible to reliably avoid the center part where shrinkage cavities easily occur and efficiently capture images of the fracture surface at the two ends where the probability of shrinkage cavities being present is relatively low. As a result, it becomes possible to secure a greater area of the measurement regions and more accurately measure the number of oxides, pieces of film, or other nonmetallic inclusions from the fracture surfaces of a predetermined number of cast sample pieces.

In another preferred embodiment of the first aspect of the invention, the area of the measurement regions is made ½ of the area of the fracture surface.

According to this embodiment, since the area of the measurement regions is ½ of the area of the fracture surface, the center where shrinkage cavities easily occur can be reliably avoided and images of the fracture surface at the two ends where the probability of shrinkage cavities being present is relatively low can be efficiently captured.

In another preferred embodiment of the first aspect of the invention, a plurality of the fracture surfaces are arranged adjoining each other at their long sides and in substantially the same plane and their fracture surfaces are simultaneously set with measurement regions.

According to this embodiment, since the fracture surfaces of the plurality of the cast samples are arranged on substantially the same plane, the measurement regions can be simultaneously set at the plurality of fracture surfaces, the accuracy of measurement of the number of nonmetallic inclusions can be secured, and the efficiency of measurement can be improved. In the old K-mold method, a cast sample taken from a K-mold (casting mold) was hammered etc. to break it into several cast sample pieces, but at that time there was the problem that highly flat fracture surfaces could not be obtained.

Regarding this point, with the new K-mold method, the K-mold (casting mold) is provided with projections, so notches are made at suitable locations of the cast sample and cast sample pieces having highly flat fracture surfaces can be obtained.

In another preferred embodiment of the first aspect of the invention, the plurality of fracture surface are fit in a case and fastened and images of the measurement regions are captured in that state.

According to this embodiment, since images of the measurement regions are captured in the state with the plurality of fracture surfaces fit into a case, it is possible to secure the accuracy of measurement of the number of nonmetallic inclusions and possible to make the measurement more efficient.

In another preferred embodiment of the first aspect of the invention, as the threshold values for digitalization and extraction of the nonmetallic inclusions, the color density amounts H, S, and V and the number of pixels are used.

According to this embodiment, the color density amounts H, S, and V and the number of pixels are used as the threshold values for digitalization and extraction of the nonmetallic inclusions. By capturing images of the fracture surfaces of the cast sample pieces by a CCD camera or other image capturing means, then processing the images, it becomes possible to identify nonmetallic inclusions by color and size and conduct measurement close to measurement of the number of nonmetallic inclusions identified by a measurer by the naked eye.

"HSV" is one type of model defining a color space. This is used as a color sample when using a computer to draw a picture. In this HSV, the color is expressed by the hue, saturation value, and brightness value.

In another preferred embodiment of the first aspect of the invention, when digitalizing and extracting the nonmetallic inclusions, a matrix is extracted by the color density amounts H, S, and V to extract the pixel clusters of the nonmetallic inclusions.

According to this embodiment, first, the matrix is digitalized and extracted by the color density amounts H, S, and V and regions other than the matrix are deemed as regions of nonmetallic inclusions, so it is possible to more stably extract regions of nonmetallic inclusions (pixel clusters). The "matrix" in this case, as explained above, means a region of the fracture surface with no nonmetallic inclusions, that is, a region from which only nonmetallic inclusions are removed in the region of the fracture surface captured.

If digitalizing and extracting nonmetallic inclusions directly using the color density amounts H, S, V, since the nonmetallic inclusions are not uniform in color and form assemblies of various types of colors, it becomes difficult to extract pixel clusters corresponding to nonmetallic inclusions. As a result, the number of nonmetallic inclusions by automatic counting (K value) becomes a smaller value than the number of nonmetallic inclusions counted by the measurer by the naked eye (K value).

Specifically, threshold values of color density, that is, H (hue): 40 to 105, S (saturation value): 0 to 40, and V (brightness value): 190 to 255, are used to digitalize and extract only the matrix and extract other regions as regions of nonmetallic inclusions (pixel clusters).

In another preferred embodiment of the first aspect of the invention, the nonmetallic inclusions correspond to pixel clusters of 100 μm or more when converting numbers of pixels of the pixel clusters to equivalent circle diameters of the pixel clusters.

According to this embodiment, it becomes possible to remove extremely fine shrinkage cavities of less than 100 μm taken into the image as noise, and measurement closer to measurement of the number of nonmetallic inclusions where the measurer identifies inclusions by the naked eye becomes possible. In the old measurement method, the size of the nonmetallic inclusions which a measurer can identify by the naked eye is about 100 μm or so, so even in the new automatic measurement method, it is possible to secure consistency of data by employing a similar reference.

Next, FIG. 1 shows an embodiment of a casting mold for obtaining a cast sample of a second aspect of the invention. The casting mold 100 (FIG. 1(3)) is comprised of a top mold 110 having a recess 112 (FIG. 1(1)) and a bottom mold 120 provided with a sprue 122 (FIG. 1(2)) and has a substantially rectangular parallelepiped cavity extending in the melt flow direction in the state with the top mold 110 and bottom mold 120 assembled (FIG. 1(3)). At the bottom 112A of the recess 112 of the top mold 110 (FIG. 1(1)), inverted V-shaped projections 114 extending in a direction vertical to the melt flow direction are provided at equal intervals.

In one preferred embodiment of the second aspect of the invention, the inverted V-shaped projections 114 provided at the bottom 112A of the recess 112 of the top mold 110 are shaped with vertical cross-sections along the lines II-II of FIG. 1(1), as shown in FIG. 2(1), with angles α at the vertices of 45° to 90° and heights H of 0.3 to 1.0 mm.

According to this embodiment, the cast sample is formed solidified in the cavity 102. As shown in FIG. 1(4), by setting the shapes and dimensions of the V-notches 132 formed at the top surface of the cast sample 130 within suitable ranges, the cast sample pieces S1 to S6 obtained by breaking the cast sample 130 at the V-notches 132 end up with flat, relatively broad area fracture surfaces F (FIG. 2(2): cross-section along line III-III of FIG. 1(4)).

For this reason, the V-shaped projections 114 of the top mold 110 (FIG. 1(1)) are preferably shaped with angles α at the vertices (FIG. 2(1)) in the range of 45° to 90°. If the angle α is less than 45°, the effect of the V-notches 132 is superior, but due to the cast melt shrinking upon solidification, it adheres to the top mold and is no longer released, i.e., so-called "sticking" occurs, mold release takes too much time, and the work efficiency falls. Further, there is also the defect that the V-shaped projections 114 of the top mold 110 are easily broken. If the angle α exceeds 90°, the effect of the V-notches 132 drops, the locations of occurrence of cracks easily become unstable, and obtaining a flat fracture surface F becomes difficult.

The V-shaped projections 114 preferably have a height H (FIG. 2(1)) of 0.3 to 1.0 mm. If the height H is less than 0.3 mm, the effect of the V-notches 132 falls and flat fracture surfaces F are difficult to obtain. If the height H is over 1.0 mm, the effect of the V-notches 132 is superior, but the area of the fracture surface F becomes too small, so this is not preferable in terms of measurement.

In another preferred embodiment of the second aspect of the invention, the bottom mold 120 (FIG. 1(2)) is provided with an inclined base 124 with an inclination angle β of 45° to 60° for forming the sprue 122 of the casting mold 100.

According to this embodiment, since the bottom mold 120 is provided with an inclined base 124 with an inclination angle β=45° to 60° at the sprue, suitable strength is given to the flow of the melt at the time of pouring the obtained melt into the sprue 122, the melt is filled up to the tip 102T of the cavity 102, and a well shaped cast sample 130 (FIG. 1(4)) can be obtained.

If the inclination angle β of the inclined base 124 is less than 45°, the flow of the melt is not made strong enough and the drop in temperature of the melt at the inclined base 124 also becomes greater, so the melt is liable not to be filled to the tip 102T of the cavity 102. If the inclination angle β of the inclined base 124 is over 60°, the flow of the melt becomes too strong and pieces of film becomes entrained at the time of pouring the melt, so this is not preferable.

In another preferred embodiment of the second aspect of the invention, the top mold 110 or bottom mold 120 has a gas relief groove (not shown) at the cavity tip 102T.

According to this embodiment, the top mold 110 or bottom mold 120 has a gas relief groove at the cavity tip 102T, so it is possible to efficiently remove from the cavity 102 any air inside the cavity 102 or hydrogen gas produced when the melt solidifies and make the melt fill up to the cavity tip 102T. Note that the top mold 110 is preferably provided with a handle (not shown) for attachment to the bottom mold 120.

Further, in general, the top mold 110 and the bottom mold 120 are provided at 116X/116Y and 126X/126Y with engagement means for positioning such as pins and pin holes enabling assembly of the casting mold 130 quickly and accurately.

EXAMPLES

Preparation of Samples

ADC12 alloy metal was melted in a 200 kg use melt/holding furnace. The melt of the holding furnace was strongly stirred whereby the pieces of film at the melt surface became entrained in the melt and the number of pieces of film increased. By further stirring of the melt, the $Al_2O_3$, MgO, spinel, or other oxide particles which had settled at the bottom of the melting furnace float up into the melt, whereby the cleanliness falls. On the other hand, by setting a long simmering holding time, the oxides, pieces of film, and other non-metallic inclusions in the melt separate by floating up or sedimentation, so the cleanliness tends to rise. By utilizing the stirring and simmering actions in this way, it is possible to suitably adjust the number (density) of oxides, pieces of film, and other nonmetallic inclusions to a certain extent.

From the melt in the holding furnace, a ladle was used to obtain about 200 g of the melt. This was suitably cast into an iron K-mold 100 as shown in FIG. 1(3). Note that the inside surface of the K-mold 100 is lightly coated in advance with a release material including boronitride (BN) by spraying etc. Further, it is preferable to preheat the casting mold 100 to about 150° C. to evaporate and dry off the solvent of the release material or moisture.

As shown in FIG. 1(1), at the bottom 112A of the recess 112 of the top mold 110 of the K-mold (casting mold) 100, inverted V-shaped projections 114 extending in a direction vertical to the melt flow direction are provided at equal intervals. While not shown, the top mold is provided with a handle for attachment with the bottom mold.

FIG. 2(1) is a partially enlarged view of the vertical cross-section along the line II-II of FIG. 1(1). The V-shaped projections 114 had angles α of their vertices of 60° and heights H of 0.6 mm. After casting the melt, the handle of the top mold was pulled by the hand to remove the top mold and the cast sample with the V-notches solidified in the cavity is taken out.

The bottom mold 120 of the K-mold (casting mold) 100 is provided with an inclined base 124 of the inclination angle β=50° at the sprue 122. Due to this inclined base 124, occurrence of film entrainment at the time of pouring the melt is suppressed, the flow of melt is given suitable strength when pouring the obtained melt into the sprue 122, the melt is filled to the tip 102T of the cavity 102, and a well shaped cast sample 130 can be obtained.

Further, the top mold 110 is provided with two gas relief grooves (not shown) at the cavity tip 102T. Due to these gas relief grooves, air filled in the cavity 102 and the hydrogen gas produced when the melt solidifies can be efficiently removed from the cavity 102 and the melt can be easily filled up to the cavity tip 102T.

The cast sample 130 is hammered along the five V-notches 132 to break it into six cast sample pieces S1 to S6. This breaks down into the sample piece S1 at the sink head R side of the cast sample 130 (single fracture surface: sink head R cut off to adjust shape to one similar to other sample pieces), a sample piece S6 of the tip 102T side (single fracture surface), and intermediate sample pieces S2 to S5 (total four, two fracture surfaces each), for a total number of fracture surfaces=1+4×2+1=10 fracture surfaces. By using V-notches 132 of suitable shapes and dimensions, it is possible to break the cast sample and obtain flat fracture surfaces F. Five of these six cast sample pieces S1 to S6 were bundled at the long sides so that their cast skins were in contact, then the five fracture surfaces were arranged in the same plane, fit in a case, and fastened. Here, the bundled five cast sample pieces included the sample piece S1 at the sink head side (fracture surface comprised of only one fracture surface) and four intermediate sample pieces S2 to S5 (one fracture surface among two fracture surfaces each used) as a first set (five fracture surfaces). Further, it includes the one sample piece S6 of the tip side (fracture surface comprised of only one fracture surface) and the four intermediate sample pieces S2 to S6 (using fracture surfaces at opposite sides to first set among the two fracture surfaces of the samples) as a second set (five fracture surfaces). With the first set and second set, a total of 10 fracture surfaces are measured.

<Measurement of Fracture Surface>

For measurement, the measurement system disclosed in Patent Document 2, a prior application of the assignee, is used.

Figure 3:
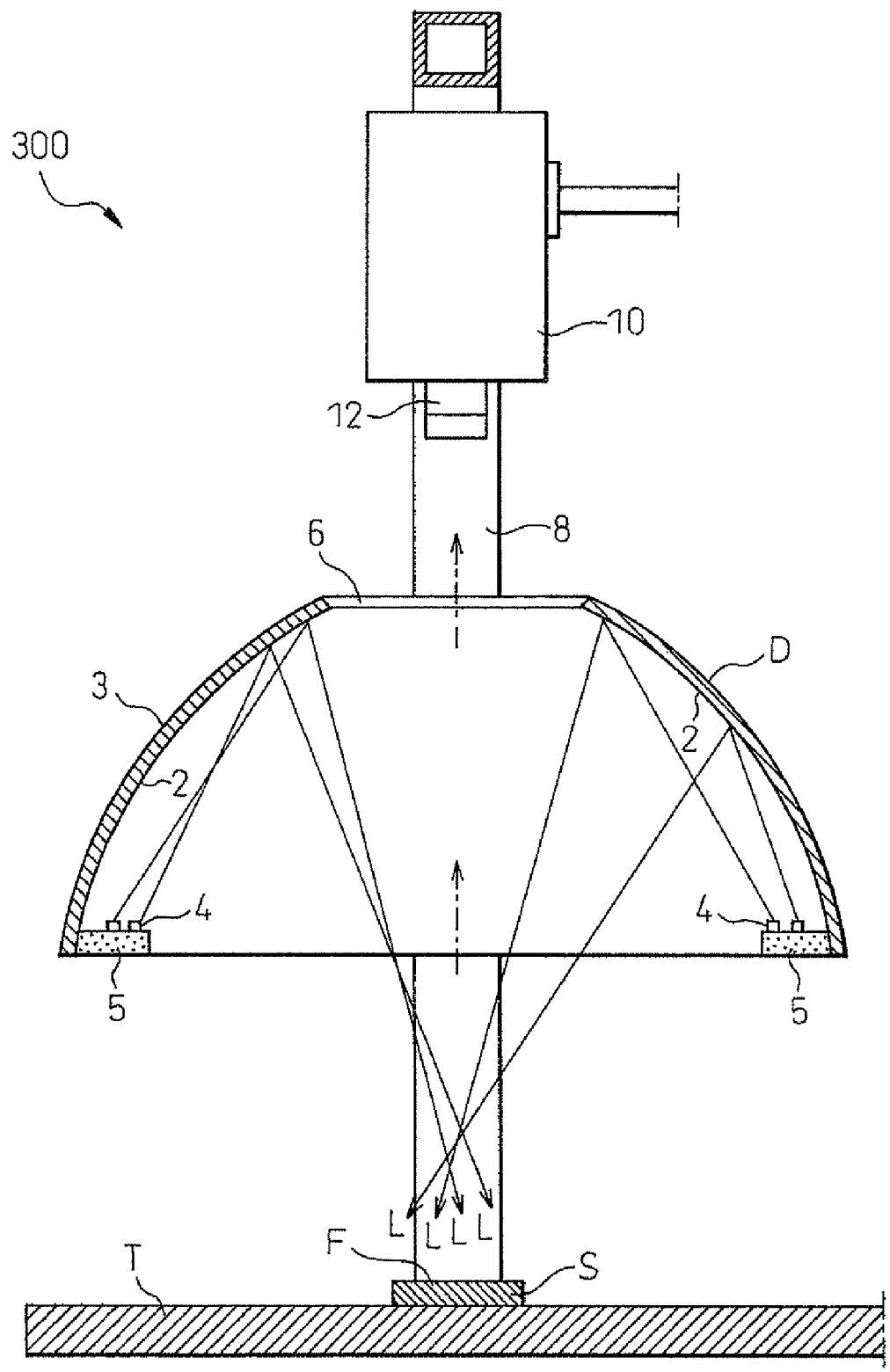
FIG. 3 is a view of the configuration of a measurement system used for the method of measurement of the present invention.

As shown in FIG. 3, the measurement system 300 includes a table T on which a sample S of aluminum having a fracture surface F is placed with its fracture surface F facing upward, a reflection dome D positioned above the table T, having a substantially semicircular cross-section, and having a downward facing concave reflection surface 2, light emitting diodes (light sources) 4 arranged along the inner edge of the concave reflection surface 2 of the reflection dome D, and a CCD camera (image capturing means) 10 arranged above an opening 6 made near the top of the reflection dome D.

The reflection dome D is attached to a pole 8 provided standing vertically from the table T so as to be able to be moved up and down through a not shown fitting. Above the reflection dome D, the CCD camera 10 is attached to a camera pole 8 in an elevatable manner. The reflection dome D has an outer circumference 3 of a substantially semicircular cross-sectional shape and a concave reflection surface 2 opening downward in a shape similar to the same. The concave reflection surface 2 is a mirror surface curved with a predetermined radius of curvature. A ring 5 attached along the inner edge of this concave reflection surface 2 is provided with a large number of light emitting diodes 4 in a ring array projecting out upward in an inside and outside row. The light emitting diodes 4 for example emit red light.

Further, near the top of the reflection dome D, an opening 6 with a quadrilateral (square or rectangular) or circular planar shape is formed. Above the opening 6, a CCD camera 10 is positioned. A barrel 12 housing this optical lens is oriented to the fracture surface F of the aluminum sample S arranged on the surface of the table T through the opening 6.

As shown in FIG. 4, the five cast sample pieces (for example S1 to S5) are fit into a case 200 like the above first set and fastened to the case 200 by screws 202 to obtain a sample S, the sample S is fastened under the reflection dome D of the measurement system 300 shown in FIG. 4 with the measured fracture surface side facing upward, and a CCD camera 10 provided at the top is used to simultaneously capture the images of the five fracture surfaces F.

Next, five cast sample pieces (in this embodiment, S2 to S6) are fit into a case 200 like the above second set and fastened to the case 200 by screws 202 to obtain another sample S, the sample S is fastened under the reflection dome D of the measurement system 300 shown in FIG. 4 with the measured fracture surface side facing upward, and a CCD camera 10 provided at the top is used to simultaneously capture the images of the five fracture surfaces F. That is, with one image capturing operation, the images of five fracture surfaces are fetched. Since the first set and second set of cast samples include a total of 10 fracture surfaces, two image capturing operations of the CCD camera become necessary.

When using the above CCD camera 10 to capture images, two modes are prepared. One mode is the case where an image of the entire fracture surface is captured (comparative example: conventional automatic measurement method), while the other mode is the case where end edges of the fracture surfaces are detected and suitable measurement regions are automatically set at the two ends of the fracture surfaces (example: automatic measurement method of the present invention). In the latter case, as shown in FIG. 4, each fracture surface F (cross-sectional area: 36 mm×5.4 mm=194.4 mm$^2$) is provided with one measurement region M at each of its two ends, that is, a total of two (total cross-sectional area: 12.15 mm×4 mm×2 locations=97.2 mm$^2$). The total area of the measurement regions by one image capturing operation of the CCD camera 10 in this case is set to an area (486 mm$^2$) of ½ of the total area of the five fracture surfaces (972 mm$^2$). The six cast samples S1 to S6 have a total of 10 fracture surfaces as explained above, so two image capturing operations by the CCD camera becomes necessary. The area (972 mm$^2$) of ½ of the total area of the 10 fracture surfaces (1944 mm$^2$) becomes the total measurement region.

Next, the images obtained by the two image capturing operations of the CCD camera are digitalized using the color density amounts H, S, and V and number of pixels (n). The inventors analyzed the color of the images of the nonmetallic inclusions in the images of the large number of fracture surfaces and discovered the threshold values of the color density amounts H, S, and V for differentiating the images of the nonmetallic inclusions and fracture surface matrix by color. Specifically, as explained above, the threshold values of the color density, that is, the H (hue): 40 to 105, S (saturation value): 0 to 40, V (brightness value): 190 to 255 are used to first digitalize and extract only the matrix so as to extract other regions as the regions of nonmetallic inclusions (pixel clusters). After this, the number of pixel clusters with 10 or more pixels in the total measurement region (972 mm$^2$) (of 100 μm or more converted to equivalent circle diameter) is calculated.

In the old measurement method, when a skilled worker counted the number of nonmetallic inclusions, he counted the pixel clusters of a size of 0.1 mm or more present at 10 fracture surfaces. Therefore, in the present invention as well, among the pixel clusters digitalized and extracted by the threshold values of the color density amounts H, S, and V, the pixel clusters with an equivalent circle diameter (D) of 100 μm or more are extracted so as to secure consistency with the count by the old measurement method. At the same time, by removing fine pixel clusters, it was possible to remove the fine shadows formed at the fracture surfaces as noise.

Here, a "pixel cluster" means a region where adjoining pixels are connected. Even when the pixels themselves are arranged in a line vertically, horizontally, or in a slant on the screen, this is recognized as a single pixel cluster. That is, the pixels may be narrow fiber shapes like with the cross-section of a film-like inclusion when viewed two-dimensionally or may be irregular triangular shapes, diamond shapes, or circular shapes. As special cases, a pixel cluster may include a blank region of pixels. So long as the blank region is surrounded by pixels and the blank region is not connected to the outside matrix, the pixel cluster is treated as being integral even if including this blank region. Here, a "matrix" means a region of the fracture surface with no nonmetallic inclusions, that is, a region excluding only nonmetallic inclusions in the region of the fracture surface captured. Here, n: number of pixels in one pixel cluster, s: actual area per pixel, and D: equivalent circle diameter of one pixel cluster are in the following relationship:

$$n \times s = \pi (D/2)^2$$

S is the actual area at the fracture surface per pixel. This is a value determined by the power of the lens used for capture by the CCD camera and the number of CCDs.

Further, a skilled worker counted the number of nonmetallic inclusions in the entire region of the 10 fracture surfaces of the five cast samples. The skilled worker used a 10× magnifying glass to observe the entire region of 10 fracture surfaces and, while eliminating shrinkage cavities, count the number of nonmetallic inclusions of a size of 0.1 mm or more ($K_{10}$ value).

Measurement Results

Example

Results of Automatic Counting by Present Invention Method

TABLE 1

|  | Old measurement method K10 value (skilled worker) | New automatic measurement method Invention example Measurement region - two ends 1/2 (count × 1) | New automatic measurement method Invention example Measurement region - two ends 1/2 (count × 2) |
|---|---|---|---|
| Sample No. 1 | 2 | 2 | 4 |
| Sample No. 2 | 1 | 1 | 2 |
| Sample No. 3 | 2 | 1 | 2 |
| Sample No. 4 | 4 | 1 | 2 |
| Sample No. 5 | 0 | 0 | 0 |
| Sample No. 6 | 1 | 0 | 0 |
| Sample No. 7 | 0 | 0 | 0 |
| Sample No. 8 | 0 | 0 | 0 |

TABLE 1-continued

| | Old measurement method K10 value (skilled worker) | New automatic measurement method Invention example Measurement region - two ends 1/2 (count × 1) | New automatic measurement method Invention example Measurement region - two ends 1/2 (count × 2) |
|---|---|---|---|
| Sample No. 9 | 0 | 0 | 0 |
| Sample No. 10 | 6 | 3 | 6 |
| Sample No. 11 | 0 | 0 | 0 |
| Sample No. 12 | 9 | 4 | 8 |
| Sample No. 13 | 0 | 0 | 0 |
| Sample No. 14 | 4 | 1 | 2 |
| Sample No. 15 | 4 | 2 | 4 |
| Sample No. 16 | 5 | 3 | 6 |
| Sample No. 17 | 2 | 1 | 2 |
| Sample No. 18 | 3 | 2 | 4 |
| Sample No. 19 | 14 | 6 | 12 |
| Sample No. 20 | 0 | 0 | 0 |
| Sample No. 21 | 0 | 0 | 0 |
| Sample No. 22 | 6 | 2 | 4 |
| Sample No. 23 | 2 | 1 | 2 |
| Sample No. 24 | 0 | 0 | 0 |
| Sample No. 25 | 2 | 1 | 2 |
| Sample No. 26 | 2 | 1 | 2 |
| Sample No. 27 | 7 | 2 | 4 |
| Sample No. 28 | 2 | 1 | 2 |
| Sample No. 29 | 2 | 1 | 2 |
| Sample No. 30 | 8 | 4 | 8 |
| Sample No. 31 | 4 | 2 | 4 |
| Sample No. 32 | 0 | 0 | 0 |
| Sample No. 33 | 6 | 4 | 8 |
| Sample No. 34 | 12 | 4 | 8 |
| Sample No. 35 | 6 | 4 | 8 |
| Sample No. 36 | 4 | 2 | 4 |
| Sample No. 37 | 9 | 5 | 10 |
| Sample No. 38 | 0 | 0 | 0 |
| Sample No. 39 | 2 | 1 | 2 |
| Sample No. 40 | 11 | 4 | 8 |
| Sample No. 41 | 0 | 1 | 2 |
| Sample No. 42 | 0 | 0 | 0 |
| Sample No. 43 | 11 | 4 | 8 |
| Sample No. 44 | 7 | 3 | 6 |
| Sample No. 45 | 4 | 3 | 6 |

Table 1 shows the results of measurement of the number of nonmetallic inclusions by the old measurement method and the results of measurement of the number of nonmetallic inclusions at the two ends of the fracture surfaces by the image processing system (½ of total area of 10 fracture surfaces). In this table, data of 45 samples from Sample No. 1 to Sample No. 45 are displayed.

In the old measurement method, a skilled worker used a 10× magnifying glass to observe the total area of 10 fracture surfaces of each cast sample (sample comprised of five cast pieces bound together) and count the number of oxides, pieces of film, or other nonmetallic inclusions of a size of 100 μm or more ($K_{10}$ value).

In the novel automatic measurement method according to the present invention, an image processing system is used to narrow down the measurement regions to the two ends of the fracture surfaces for each cast sample, capture images of ½ the area of the five fracture surfaces of five cast samples by a CCD camera, process the captured image for color density, and digitalize and extract the matrix by predetermined H, S, and V amounts to extract the regions of nonmetallic inclusions (pixel clusters), and count the number of pixel clusters with an equivalent circle diameter of 100 μm or more. This operation was repeated two times for the front and rear of the cast samples to count the number of nonmetallic inclusions of a total of 10 fracture surfaces. The count region is ½ of the entire fracture surface area of 10 fracture surfaces, so the value of this count doubled is also shown in Table 1.

Figure 5:
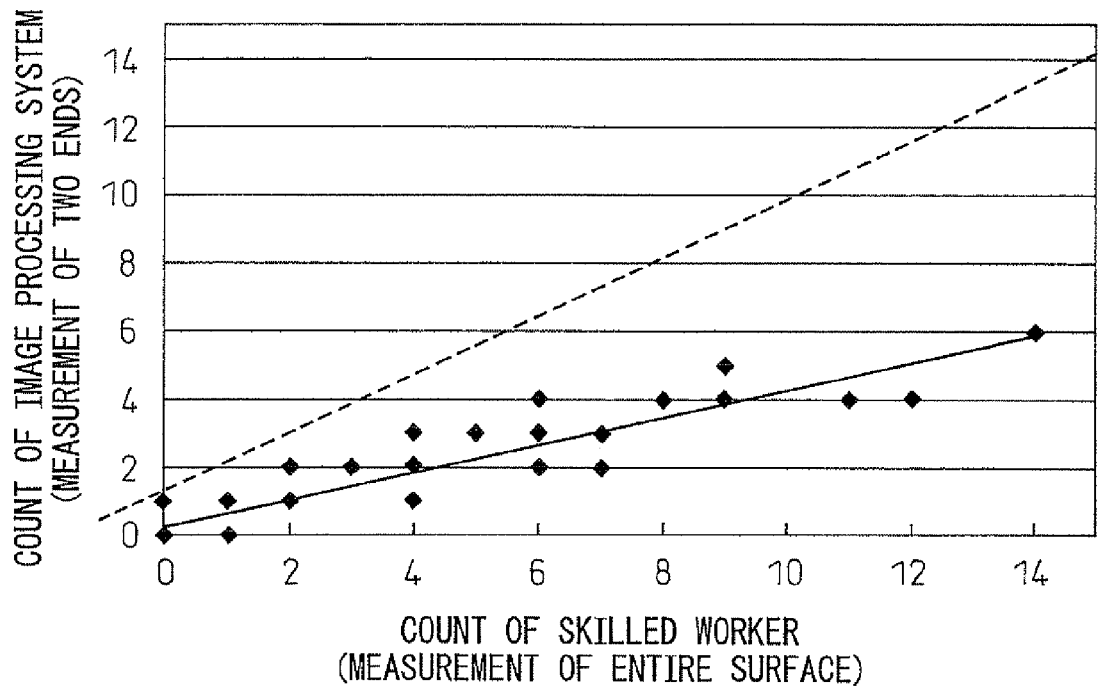
FIG. 5 is a graph showing the correlation between a value measured by an automatic measurement method of the present invention and a value measured by a skilled worker.
Figure 6:
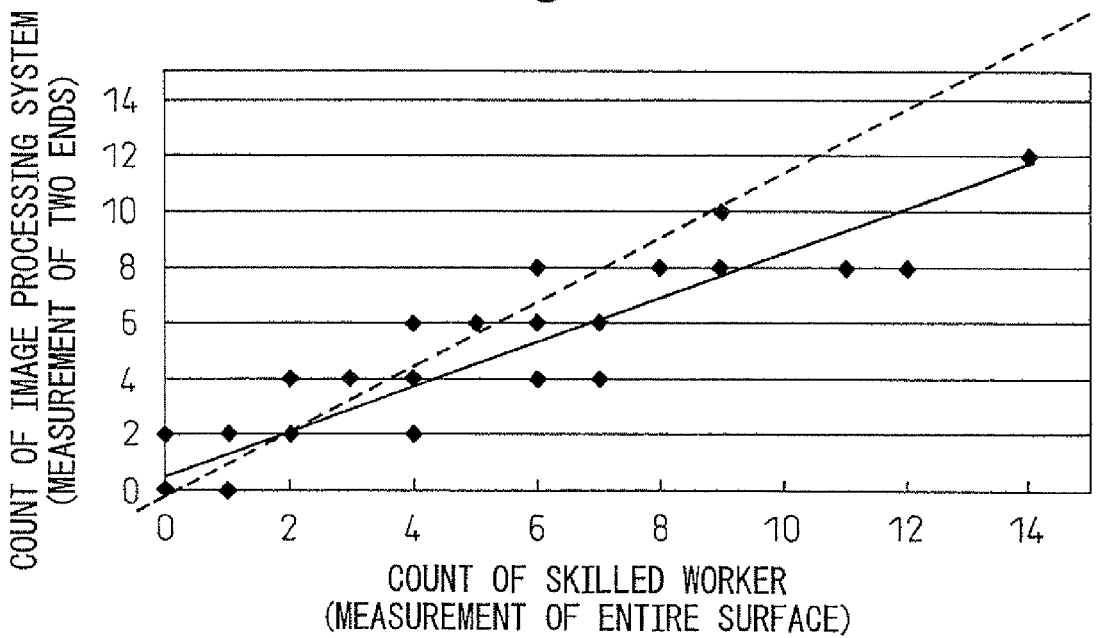
FIG. 6 is a graph showing the correlation between a value measured by an automatic measurement method of the present invention doubled and a value measured by a skilled worker.

FIG. 5 shows the correlation between the count of a skilled worker and the count (count×1) of an image processing system. Further, FIG. 6 shows the correlation between the count of a skilled worker and the count (count×2) of an image processing system. From FIG. 5 and FIG. 6, it is learned that there is a strong positive correlation between the count ($K_{10}$ value) of the number of nonmetallic inclusions obtained by a skilled worker using a 10× magnifying glass to observe the entire fracture surface and the count of the new automatic measurement method of the present invention using an image processing system. This shows that a skilled worker can instantaneously eliminate the fine cavities which easily occurred at the center of the fracture surface, while the new automatic measurement method using an image processing system captures images of only the regions at the two ends of the fracture surface where there is little occurrence of fine cavities and digitalizes them by predetermined threshold values to count the number of pixel clusters, so the count is resistant to the effects of fine cavities.

Comparative Example

Results of Automatic Count by Conventional Method

TABLE 2

|  | Old measurement method K10 value (skilled worker) | Conventional automatic measurement method Comparative example Measurement region - entire region of fracture surface (count × 1) |
|---|---|---|
| Sample No. 1 | 2 | 8 |
| Sample No. 2 | 1 | 10 |
| Sample No. 3 | 2 | 3 |
| Sample No. 4 | 0 | 0 |
| Sample No. 5 | 0 | 8 |
| Sample No. 6 | 1 | 0 |
| Sample No. 7 | 0 | 4 |
| Sample No. 8 | 7 | 8 |
| Sample No. 9 | 0 | 3 |
| Sample No. 10 | 6 | 15 |
| Sample No. 11 | 0 | 4 |
| Sample No. 12 | 9 | 5 |
| Sample No. 13 | 0 | 2 |
| Sample No. 14 | 4 | 8 |
| Sample No. 15 | 4 | 16 |
| Sample No. 16 | 5 | 3 |
| Sample No. 17 | 2 | 8 |
| Sample No. 18 | 3 | 2 |
| Sample No. 19 | 8 | 15 |
| Sample No. 20 | 7 | 2 |
| Sample No. 21 | 0 | 8 |
| Sample No. 22 | 1 | 5 |
| Sample No. 23 | 4 | 4 |
| Sample No. 24 | 10 | 18 |
| Sample No. 25 | 3 | 3 |

Table 2 shows the results of measurement of the number of nonmetallic inclusions by the old measurement method and the results of measurement of the number of nonmetallic inclusions of the total fracture surfaces (total area of 10 fracture surfaces) by an image processing system. In this table, the data of 25 samples from Sample No. 1 to Sample No. 25 is displayed.

In the same way as the case of the examples, in the old measurement method, a skilled worker used a 10× magnifying glass to obtain the total area of 10 fracture surfaces for each cast sample (each sample comprised of five cast pieces bundled together) to count the number of oxides, pieces of film, or other nonmetallic inclusions of a size of 100 μm or more.

In the conventional automatic measurement method, an image processing system is used to detect the edges for each cast sample (entire region of one fracture surface), set a rectangular shaped measurement region, capture an image of that region by a CCD camera, process the captured image by the color density, digitalize it by predetermined H, S, V values, and count the number of pixel clusters with an equivalent circle diameter of 100 μm or more. This operation is repeated 10 times to count the number of nonmetallic inclusions of the entire area of the 10 fracture surfaces. The captured fracture surface area is the total fracture surface area, so this count is described in Table 2.

Figure 7:
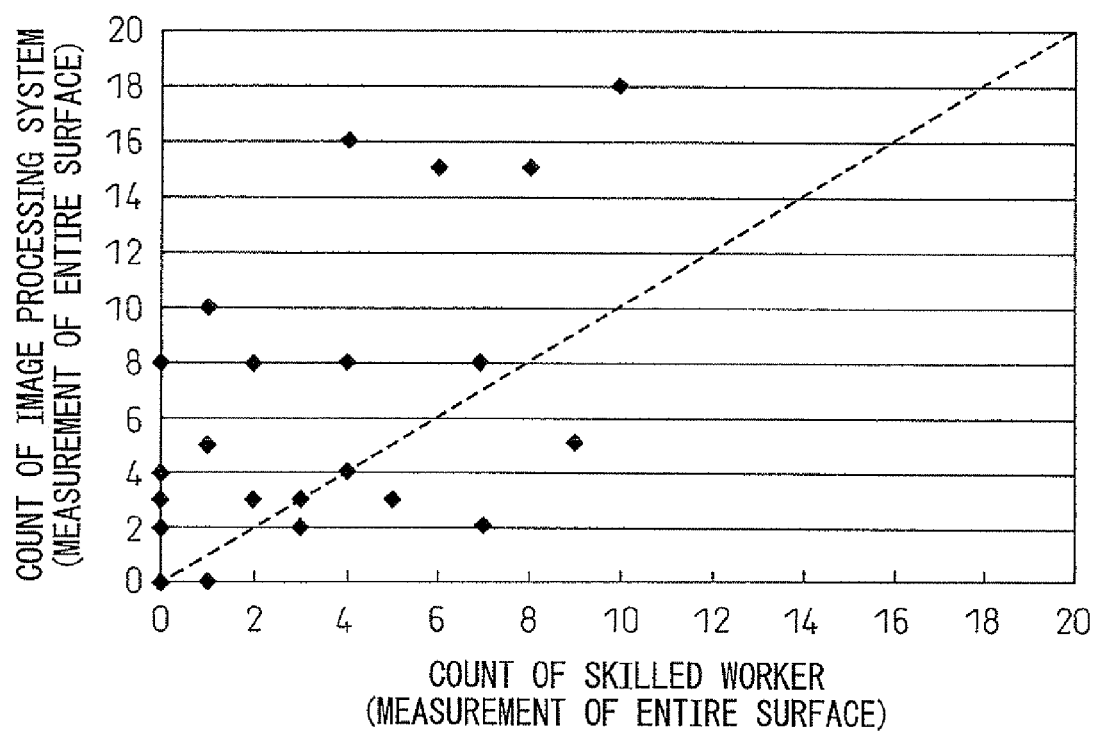
FIG. 7 is a graph showing the correlation between a value measured by a conventional automatic measurement method and a value measured by a skilled worker.

FIG. 7 shows the correlation between a count by a skilled worker and a count (count×1) by an image processing system. From FIG. 7, it is learned no correlation is recognized or there is only an extremely weak correlation between the count of the number of nonmetallic inclusions obtained by a skilled worker using a 10× magnifying glass to observe the entire fracture surface ($K_{10}$ value) and the count by the conventional automatic measurement method using an image processing system. This shows that a skilled worker can instantaneously eliminate the fine cavities which easily occurred at the center of the fracture surface, while a conventional automatic measurement method using an image processing system captures an image of the entire fracture surface region and digitalizes it by predetermined threshold values to count the number of pixel clusters, so the count is affected by the fine cavities which easily occur at the center of the fracture surface.

INDUSTRIAL APPLICABILITY

According to the present invention, there are provided a method of automatically counting the number of inclusions by eliminating the effects of shrinkage cavities in the conventional automatic measurement method and securing a high correlation with the value measured by a skilled worker and a casting mold for obtaining a cast sample used for the same.

The invention claimed is:

1. A method of measurement of the number of nonmetallic inclusions in a rectangular fracture surface of a cast sample comprising:
   capturing an image of a rectangular fracture surface of a cast sample comprised of an aluminum alloy by a CCD camera or other image capturing means, said rectangular fracture surface having short sides and long sides, respectively,
   processing the image captured by said image capturing means for color density, digitalizing the resultant processed image by a predetermined threshold value, and counting the number of pixel clusters of a predetermined size or more within the digitalized, processed image,
   wherein, before said capturing of the image, the end edges of the short sides of said rectangular fracture surface are detected and then measurement regions of an area of ¼ to ⅔ of the area of said fracture surface at the two ends of said fracture surface are automatically set.

2. A method of measurement of the number of nonmetallic inclusions as set forth in claim 1, wherein a plurality of said measurement regions are set at an inside of said fracture surface and are rectangular in shape.

3. A method of measurement of the number of nonmetallic inclusions as set forth in claim 1, wherein the area of said measurement regions is ½ of the area of said fracture surface.

4. A method of measurement of the number of nonmetallic inclusions as set forth in claim 1, wherein a plurality of said fracture surfaces are arranged adjoining each other at their long sides and in substantially the same plane and their fracture surfaces are simultaneously set with measurement regions.

5. A method of measurement of the number of nonmetallic inclusions as set forth in claim 4, wherein said plurality of fracture surface are fastened by being fit in a case and images of said measurement regions are captured in that state.

6. A method of measurement of the number of nonmetallic inclusions as set forth in claim 1, wherein as threshold values for digitalizing and extracting said nonmetallic inclusions, color density amounts H, S, and V and a number of pixels are used.

7. A method of measurement of the number of nonmetallic inclusions as set forth in claim 6, wherein when digitalizing and extracting said nonmetallic inclusions, a matrix is extracted by color density amounts H, S, and V to extract said pixel clusters of said nonmetallic inclusions.

8. A method of measurement of the number of nonmetallic inclusions as set forth in claim 6, wherein said nonmetallic inclusions correspond to pixel clusters of 100 μm or more when converting numbers of pixels of the pixel clusters to equivalent circle diameters of the pixel clusters.

9. A method of measurement of the number of nonmetallic inclusions according to claim 1, wherein a plurality of the cast samples are obtained from an initial cast sample formed in a casting mold comprising a top mold having a recess and a bottom mold having a sprue, having a substantially rectangular parallelepiped cavity extending in the melt flow direction in the state where the top mold and said bottom mold are assembled, and provided, at equal intervals at the bottom of the recess of the top mold, with inverted V-shaped projections extending in a direction vertical to the melt flow direction, whereby said V-shaped projections form notches in the resultant initial cast sample, and the initial cast sample is then fractured at each of the notches to form a plurality of said cast samples with flat fracture surfaces.

10. A method of measurement of the number of nonmetallic inclusions according to claim 9, wherein said V-shaped projections are shaped with an angle at the vertices in a range of 45° to 90° and said V-shaped projections have a height of 0.3 to 1.0 mm.

11. A method of measurement of the number of nonmetallic inclusions according to claim 9, wherein said bottom mold having a sprue is provided with an inclined base having an inclination angle of 45° to 60° at its sprue.

* * * * *